United States Patent [19]
Garcia y Bellon et al.

[11] Patent Number: 4,971,951
[45] Date of Patent: Nov. 20, 1990

[54] INSULIN POTENTIATION THERAPY

[76] Inventors: Donato P. Garcia y Bellon, Ponciano Arriaga No. 28, 06030 Mexico City, D. F., Mexico; Donato P. Garcia, Jr., Fuente De Marcela #33, 5390 Nancalpan, Mexico, 5390; Steven G. Ayre, 1481 Regent Road, Montreal, Quebec H3P-211, Canada

[21] Appl. No.: 77,833

[22] Filed: Jul. 27, 1987

[30] Foreign Application Priority Data

Jun. 15, 1987 [CA] Canada ................................ 539,603

[51] Int. Cl.$^5$ ........................................... A61K 37/26
[52] U.S. Cl. ........................................... 514/3; 514/4
[58] Field of Search ........................................ 514/3, 4

[56] References Cited

U.S. PATENT DOCUMENTS 2,145,869  2/1939  Garcia .................................. 514/23

Primary Examiner—Nathan M. Nutter
Attorney, Agent, or Firm—Melvin K. Silverman

[57] ABSTRACT

A new method of treatment of viral diseases, such as cancers and AIDS by intravenous injection of insulin to induce hypoglycemia, followed by parenteral injection of glucose, mixed with or in conjunction with, prescribed anti-viral/antineoplastic drugs. The composition of the adjuvant and therapeutical drugs are also disclosed.

19 Claims, No Drawings

INSULIN POTENTIATION THERAPY

BACKGROUND OF THE INVENTION

1. Field of the Invention

This invention relates generally to a new method of treatment of viral diseases. More specifically, this invention relates to a method employing a new adjuvant for treating viral diseases, and new compositions for carrying out such treatment.

2. Description of Prior Art

Various carriers, adjuvants or agents have been used to enhance the absorption or to potentiate the effect of drugs administered to patients for treatment of specific diseases. An adjuvant to potentiate insulin for treatment of diabetes has been disclosed in U.S. Pat. No. 4,277,465. U.S. Pat. No. 4,196,196 discloses a composition of insulin, glucose and magnesium dipotassium ethylene diamine tetraacetic acide to enhance tissue perfusion and to facilitate a divalent/monovalent cation gradient. A third U.S. Pat. No. 2,145,869, discloses a composition including insulin and glucose for treatment of syphylis.

However, it has not heretofore been known to treat viral diseases by administration to a patient of insulin to induce hypoglycemia, followed by administration of glucose and a specific drug directed at the treatment of a viral deasease, nor have compositions for such treatment been disclosed.

SUMMARY OF THE INVENTION

This invention relates to a novel method of treatment of viral diseases on an intracellular level by inducing hypoglycemia by administration of insulin and subsequent administration, during the state of hypoglycemia, of glucose and a specific prescribed drug directed at a specific viral disease.

This invention also relates to a method of treatment of viral diseases by administering drugs in lower dosages than would ordinarily be required for effective treatment in the absence of the insulin/glucose treatment of this invention.

The present invention relates to the treatment of diseases such as are considered by the state of the art in medical understanding to be virally-related, and in which the cells involved in these disease processes are said to be virally-affected. For the purposes of this invention, a virally affected cell is one that has been induced into malignant transformation (cancer) by the action of a virus, or has been directly infected and functionally destroyed by a virus. According to this present definition of terms, the term "antiviral drug" is broadened in its scope to include the variety of antineoplastic or anticancer drugs. The present invention specifies but is not limited to the above described virally related disease processes.

The present invention further relates to treatment of specific viral diseases such cancers and acquired immune deficiency syndrome (AIDS).

This invention in one aspect relates to a systemic adjuvant for potentiating the drug to be effectively absorbed by the virally infected cells, which comprises insulin and glucose and in another aspect, to new compositions of said adjuvant and the drug prescribed for the particular disease.

DETAILED DESCRIPTION OF THE INVENTION

It is well known that the hormone insulin regulates the carbohydrate metabolism, the synthesis of protein and of RNA, and the formation and storage of neutral lipids. Thus synthetic insulin is administered to the diabetic patients to aid the metabolism of glucose. It has now been found that insulin also increases cell membrane permeability. The treatment of the present invention is thus named Insulin Potentiation Therapy, hereinafter referred to as IPT.

Experimental observations support a theory that insulin will enhance the permeability of cell membranes to glucose and other sugars. Moreover, this increased permeability is not limited to sugars, but includes other solutes such as drugs. This increased permeability induced by insulin furthermore permits the removal of waste products from intracellular fluid (ICF) into the extracellular fluid (ECF), and more importantly, to transfer the drug molecules from the ECF to the ICF, thus potentiating the effects of administered drug.

It has also been found that in viral diseases such as various cancers and AIDS, the viral cells in the active growth stage are most receptive to drugs. Therefore, it is most effective to treat the disease at this stage.

It has been established that the virally affected cells targeted for treatment in IPT (cancer cells for malignancy; lymphocytes and brain cells for AIDS) possess insulin receptors on their cell membranes. Thus these cells would be amenable to insulin's potentiating effect. It is to be understood that the virally affected cells herein referred to include cancer cells as well as cells susceptible to attack by the AIDS virus (human immunodeficiency virus-HIV) which includes principally the aforementioned lymphocytes (specifically the $T_4$ helper subset of lymphocytes) and brain cells.

In accordance with the present invention, a systemic adjuvant is defined as an adjuvant to potentiate the migration of a drug through cell membranes, which includes insulin in the amount of one unit per 10 kg of body weight to induce a mild state of hypoglycemia, and a dose of glucose in the amount of about 20–50 cc of 50% hypertonic glucose.

The insulin used in the IPT treatment is regular crystalline insulin solution, 100 units/cc. The glucose may either be injected as a mixture with the drug, or separately immediately before injection of the prescribed drug.

The effect of the IPT treatment is two-fold: first, the cell membranes of the virally affected cells are rendered more permeable by the insulin and thus more receptive to the administered drugs; secondly, the administered glucose in one aspect, restores the patient's glucose equilibrium and, in another aspect, maximizes absorption of the drug through the cell membranes by virtue of the ECF to ICF diffusion gradient this hypertonic glucose injection causes. It has been demonstrated by in vitro experiments with human breast cancer cells that the cytotoxic effect of the antineoplastic drug methothrexate is increased ten-thousand-fold when used in conjunction with insulin. Breast cancer cells also showed an increased capacity to accumulate free intracellular methothrexate in the presence of insulin.

Ribavirin is an antiviral agent that has been used in the treatment of early HIV infection (lymphadenopathy syndrome, AIDS-Related-Complex, or ARC). These are considered to be pre-AIDS conditions. Used in the conventional way, ribavirin has not been found effective in the treatment of established AIDS disease. This is because effective concentrations of drug within the brain only develop after long term therapy when toxic side effects start to play a limiting role for the use of the drug.

Some antiviral/antineoplastic drugs currently on the market include cyclophosphamide, methotrexate and 5-flourouracil. These drugs all have toxic side effects. The most serious, sometimes fatal, side effects are immune suppression, anemia and gastrointestinal homorrhage. Therefore, the use of these antineoplastic drugs involves high risk. IPT, in accordance with the present invention, reduces such risks because under the effect of insulin, the antiviral drug dosage may be greatly reduced.

The following table shows a comparison of drug dosages with IPT and with that of conventional treatment.

| Drug | Dosage with IPT | Conventional dosage |
| --- | --- | --- |
| ribavirin | one treatment - 30 mg IV plus 200 mg tablet orally daily for 6 days total - 1,230 mgs/week | 400 mg tablets twice per day for 7 days total - 5,600 mg/week |
| cyclophosphamide | one treatment - 50-100 mg IV plus 100 mg tablet daily for 6 days total - 650-700 mg in 7 days | total - 3,500 mg in 5 days |
| methothrexate | one treatment - 1.25-2.5 mg IV plus 2.5 mg tablet daily for 6 days total - 16.25-17.5 mg in 7 days | 10-25 mg tablet daily for 7 days total - 70-175 mg in 7 days |
| 5-flourouracil | one treatment - 4 mg IV plus 4 mg tablet daily for 6 days total - 28 mg/7 days | 84 mg daily for 4 days total - 326 mg/4 days |

The above table is based on body weight, 70 kg.

The method of treatment, in general, involves administering a dose of 4-8 units of insulin, more specifically, one unit of insulin per 10 kg of body weight, by intravenous (IV) injection. The patient is in the fasting state. The patient is closely observed for insulin side effects. After 20 minutes of observation, and establishment of induced hypoglycemia, 20-50 cc of 50% of hypertonic glucose is injected intravenously in conjunction with, or mixed with, the prescribed drug in the dosage described above.

The potentiation of antiviral drug therapy is the primary intent of IPT treatments. Other drugs directed at the simple alleviation of the symptoms of disease may also be given during treatments. These drugs too are given in reduced dosages, orally, intramuscularly, and intranvenously, 20 minutes after the insulin injection. In addition to the drugs necessary for treatment of viral infection, nutritional supplements such as minerals, and vitamins may be administered to the patient. The IPT treatment is given weekly followed by evaluation and testing to determine the progress of the treatment. Between treatments, the patient is given oral antiviral antineoplastic drug for the six days while resting at home.

The application of IPT to the specific diesase, AIDS, has just been tested in clinical cases. It has been established that the AIDS virus causes a profound disruption of the immune system by infecting and inactivating the $T_4$ helper lymphocyte population. The AIDS virus also affects brain tissue, which has important implications for the persistence of the disease in infected human beings. As described elsewhere, IPT is ideally suited to overcoming this special problem in AIDS.

Thus far, only a handful of anti-AIDS drugs have been tested with various degrees of success: azidothymidine, Ribavirin, Suramin and HPA-23. The primary mode of action of these drugs is the blocking of the enzyme Reverse Transcriptase, which enzyme is necessary for replication of the AIDS virus.

The present invention greatly improves the efficacy of such drug treatment by potentiating the drug with insulin and glucose, thus reducing the required drug dosage and toxicity and allows prolonged treatment with the drug. Most importantly for AIDS, IPT allows these drugs free access to the AIDS virus infecting the brain tissue. Erradication of this focus of virus is essential for complete treatment of AIDS.

The IPT treatment for AIDS is similar to that outlined above with respect to cancer therapy. Insulin is administered intravenously first, followed by administration of glucose and an effective amount of anti-AIDS drug. Additional antibiotic and antineoplastic drugs may be concurrently administered. The treatment is carried out weekly, but may be carried out twice a week when necessary. Oral drugs are taken daily during the remaining days of the week.

The systemic adjuvant, one unit/10 kg body weight of insulin and 20-50 cc of 50% hypertonic glucose as described hereinbefore, in combination with an antiviral drug, whether it be antineoplastic or anti-AIDS, constitutes a new composition for treatment of virus disease.

It should be noted that not every patient is a candidate for IPT treatment. Pregnant women, diabetics and children under the age of three are not suitable patients for such treatment.

The IPT treatments are now described in the following clinical cases:

CASE 1: INFILTRATING ADENOCARCINOMA OF THE BREAST

A 53-year-old female had a right breast cancer since May 23, 1985 without treatment. By August, 1986, the breast cancer had developed into a swelling with foul-smelling discharge which caused pain and immobility in her right arm. She had weight loss and low-grade fever. Her weight at the time of treatment was 73.4 kg.

A series of weekly IPT treatments was initiated. Seven units of insulin was injected intravenously. After 20 minutes, she was given 50 cc of 50% of hypertonic glucose, 10 mg of cyclophosphamide and 1.25 mg of Methothrexate, by intravenous injection. For six days during the week between IPT treatments, the patient took 100 mg of cyclophosphamide orally each day. After the fifth IPT treatment, 4 mg of 5-flourouracil IV was added to the weekly drug regimen.

Concurrently in these treatments, other drugs such as antibiotics, vitamin B complex and vitamin C and calcium gluconate were also administered either orally or parenterally. After the tenth treatment, a mammogram was taken which showed a slight thickening of the skin in the right retroareolar area, no calcification or tumor masses were identified. There was some thickening of the skin of the right breast, but no palpable masses in either breast. The cervical, supraclavicular and axillary lymphadenopathy were likewise no longer palpable. The patient's right arm had returned to its normal size and color and was fully functional. The patient continued with follow-up examinations and has shown no evidence of recurrence of breast cancer since April of 1987.

CASE 2: ADENOCARCINOMA OF THE LUNG

A 45-year-old non-smoking female suffered from adenocarcinoma of the lung in the left lower lobe, classified as stage III. Weekly IPT treatment started on Nov. 12, 1985, with 6 units of insulin injected intravenously, followed by 20 cc of 50% hypertonic glucose and 1.24 mg of Methothrexate and 10 mg of cyclophosphamide. After the 8th weekly treatment, a daily tablet of 100 mg of cyclophosphamide was prescribed. A chest X-ray showed a significant reduction of the left lower lobe lesion with a disappearance of the satellite lesion. A year later, a follow-up X-ray showed almost complete clearing of the lesion in the left lower lobe of the lung.

CASE 3: CARCINOMA OF THE CERVIX

A 22-year-old female suffered from abdominal pain, dysuria, leukorrhea and intermenstrual bleeding. She was diagnosed to have a carcinoma of the cervix mixed with adenoacanthoma Grade II. Nine treatments were given once a week for nine weeks. Five units of insulin were given followed by 50 cc of 50% hypertonic glucose and 100 mg of cyclophosphamide. Antibiotics, B complex and steroid were given as needed. At the end of the ninth treatment, a Pap smear test was negative; and a biopsy indicated chronic cervicitis with leukoparakeratosis and foci of squamous metaplasia but no signs of anaplasia. Sixteen years later, a normal pregnancy and delivery were completed.

CASE 4: EWING'S SARCOMA OF THE BONE

A three-year-old female child had suffered a wrist fracture. At the time of removal of her cast, gross deformity of the distal radius on her left wrist was diagnosed as Ewing's tumor of the bone. An X-ray showed metastatic lesions were already present in other bones.

The parents of the child were told that Ewing's tumor of the bone in an advanced stage has no cure. Nevertheless, the parents brought the child for a trial IPT. IPT treatment was started with 5 units of insulin, followed by 30 mg of cyclophosphamide in conjunction with 50 cc of 50% of hypertonic glucose.

A total of seventeen weekly treatments was given. At the midpoint of the patient's treatment, her X-ray showed good bone neo-formation with reestablishment of a more normal contour to the distal radius. Upon completion of the 17th treatment, the child was clinically well and has since lived a healthy life.

CASE 5: AIDS WITH HERPES ZOSTER

A 47-year-old homosexual male had been diagnosed by two successive positive HTLV III antibody tests, to have AIDS. IPT started on Nov. 25, 1986. The patient had complaints of recurrent herpes zoster infection on the left side of his head and neck, painful cervical lymphadenopathy, fever, malaise, weekness, diarrhea, headache, irritability, poor memory, depression, and a weight loss of 15 kg over the preceding 6–8 weeks. Examination revealed single 2 cm nodes palpable in each axilla. A 2 cm node was palpable in the right groin.

On Nov. 27, 1986, IPT treatment was started twice a week. Six units of insulin were given intravenously; after a 20-minute interval, 30 mg of Ribavirin mixed with 50 cc of 50% hypertonic glucose was injected intravenously. Antineoplastic drugs, cyclophosphamide (10 mg) and Methotrexate (0.5 mg) along with vitamin B complex were concurrently administered. On non-treatment days, the patient took 200 mg Ribavirin orally, daily, along with any necessary drugs prescribed. At the end of the third treatment, the patient's fever, headaches, diarrhea, poor memory and depression disappeared. The patient reported feeling well in all respects, and has resumed his normal activities. On examination, the herpes zoster had cleared, the swellings in his neck were no longer visible, and there was no palpable lymphadenopathy in the neck, and he had gained 7 kg. As of Mar. 3, 1987, the HTLV III assay remains positive, the total $T_4$ lymphocyte count is 233, and $T_4:T_8$ ratio is 0.45. The patient remains under active treatment with regularly scheduled follow-up laboratory testing.

It is evident from the clinical cases, that the synergistic effect of insulin and glucose in potentiating the drug directed at these virally-related diseases, at a predetermined dosage is surprising and unprecedented.

Numerous modifications and variations of the present invention are possible in light of the above teaching, and therefore, within the scope of the appended claims; the invention may be practiced otherwise than as particularly described.

We claim:

1. A method for treatment of viral diseases in a human, comprising: administering to said human suffering therefrom an effective dose of insulin to induce mild hypoglycemia, and thereafter administering a predetermined dose of glucose and a prescribed anti-viral drug.

2. The method of claim 1 being carried out on a weekly basis.

3. The method of claim 1 wherein insulin is administered at a dose of one unit per 10 kg of body weight.

4. The method of claim 1 wherein said glucose is about 20–50 cc of 50% hypertonic glucose solution.

5. The method of claim 1 wherein said anti-viral drug is selected from the group consisting of cyclophosphamide, methothrexate, 5-flourouracil, azidothymidine, ribavirin, surmarin and HPA-23.

6. A systemic adjuvant for potentiation of anti-viral drug comprising an effective amount of insulin to induce hypoglycemia and a subsequent dose of glucose.

7. The systemic adjuvant of claim 6 wherein said insulin is one unit per 10 kg of body weight and said glucose is about 20–50 cc of 50% hypertonic glucose.

8. A pharmaceutical composition, comprising:
insulin-about one unit per 10 Kilogram of body weight;
glucose-fifty percent solution, in the range of about twenty to about fifty cubic centimeters; and
a prescribed amount of an anti-neoplastic drug.

9. The composition of claim 8 wherein said antineoplastic drug is selected from the group consisting of cyclophosphamide, methothrexate and 5-flourouracil.

10. A pharmaceutical composition, comprising:
insulin-about one unit per 10 kilograms of body weight;
glucose-fifty per cent solution, in the range of about twenty to about fifty cubic centimeters; and a prescribed amount of an anti-AIDS drug.

11. The composition of claim 10 wherein said anti-AIDS drug is selected from a group of azidothymidine, ribavirin, suramin and HPA-23.

12. The method of claim 1 wherein the viral disease is AIDS, and said treatment being carried out twice a week.

13. The composition of claim 9 wherein cyclophosphamide is about 50-100 mg.

14. The composition of claim 9 where methothrexate is in the amount of 1.25-2.5 mg.

15. The composition of claim 9 wherein 5-flourouracil is in the amount of 2-5 mg.

16. The composition of claim 11 wherein said ribavirin is in the amount of 30 mg.

17. The method as recited in claim 3 in which said administering step comprises the step of intravenous administration.

18. The method as recited in claim 4 in which said step of administration comprises the step of intravenous administration.

19. The method as recited in claim 5 in which said step of administering comprising the step of intravenous administration.

* * * * *